(12) United States Patent
Mihăescu et al.

(10) Patent No.: US 9,999,654 B2
(45) Date of Patent: Jun. 19, 2018

(54) COMPOSITION WITH INCREASED BIOAVAILABILITY OF ORALLY ADMINISTERED EMBRYO-PEPTIDES AND PROCESS FOR ITS OBTAINMENT

(71) Applicant: SC HIPOCRATE 2002 SERV SRL, Bucharest (RO)

(72) Inventors: Gheorghe Mihăescu, Bucharest (RO); Florin Oancea, Bucharest (RO)

(73) Assignee: SC Hipocrate 2002 SERV SRL, Bucharest (RO)

( * ) Notice: Subject to any disclaimer, the term of this patent is extended or adjusted under 35 U.S.C. 154(b) by 56 days.

(21) Appl. No.: 14/428,869

(22) PCT Filed: Sep. 17, 2013

(86) PCT No.: PCT/RO2013/000016
§ 371 (c)(1),
(2) Date: Mar. 17, 2015

(87) PCT Pub. No.: WO2014/104906
PCT Pub. Date: Jul. 3, 2014

(65) Prior Publication Data
US 2015/0224171 A1   Aug. 13, 2015

(30) Foreign Application Priority Data
Sep. 19, 2012 (RO) ................. a201200665

(51) Int. Cl.
| | |
|---|---|
| *A61K 38/17* | (2006.01) |
| *A61K 35/57* | (2015.01) |
| *A61K 9/48* | (2006.01) |
| *A61K 36/064* | (2006.01) |
| *A61K 38/18* | (2006.01) |
| *A61K 47/02* | (2006.01) |
| *A61K 47/12* | (2006.01) |
| *A61K 47/22* | (2006.01) |
| *A61K 47/24* | (2006.01) |
| *A61K 47/28* | (2006.01) |
| *A61K 47/36* | (2006.01) |

(52) U.S. Cl.
CPC ............ *A61K 38/17* (2013.01); *A61K 9/4858* (2013.01); *A61K 9/4875* (2013.01); *A61K 35/57* (2013.01); *A61K 36/064* (2013.01); *A61K 38/18* (2013.01); *A61K 47/02* (2013.01); *A61K 47/12* (2013.01); *A61K 47/22* (2013.01); *A61K 47/24* (2013.01); *A61K 47/28* (2013.01); *A61K 47/36* (2013.01)

(58) Field of Classification Search
CPC ...... A61K 35/57; A61K 36/064; A61K 38/17; A61K 38/18; A61K 47/02; A61K 47/12; A61K 47/22; A61K 47/24; A61K 47/28; A61K 47/36; A61K 9/4858; A61K 9/4875
See application file for complete search history.

(56) References Cited

U.S. PATENT DOCUMENTS

| | | | |
|---|---|---|---|
| 4,405,602 | A | 9/1983 | Ilies |
| 4,830,716 | A | 5/1989 | Ashmead |
| 4,908,206 | A | 3/1990 | Schafer et al. |
| 5,641,517 | A | 6/1997 | Eskeland et al. |
| 2011/0200737 | A1 | 8/2011 | Suyanto |
| 2012/0028891 | A1* | 2/2012 | Paetau-Robinson ... A61K 35/34 514/4.8 |

FOREIGN PATENT DOCUMENTS

| | | |
|---|---|---|
| CA | 2197050 A1 | 8/1998 |
| EP | 0929308 B1 | 8/2002 |
| RO | 107551 B1 | 5/1991 |
| RO | 119509 B1 | 12/2004 |

(Continued)

OTHER PUBLICATIONS

Rinderknecht, et al., "The Amino Acid Sequence of Human Insulin-like Growth Factor I and its Structural Homology with Proinsulin", The Journal of Biological Chemistry, vol. 253, No. 8, Issue of Apr. 25, 1978, pp. 2769-2776.

McCusker, et al., "Zinc Partitions IGFs from Soluble IGF Binding Proteins (IGFBP)-5, But Not Soluble IGFBP-4, to Myoblast IGF Type 1 Receptors", Journal of Endocrinology, 2004, 180, 227-246.

Lowry, et al., "Protein Measurement with the Folin Phenol Reagent", Journal of Biological Chemistry, vol. 193, Nov. 1951, pp. 265-275.

English Translation of RO 107551.

(Continued)

*Primary Examiner* — Lisa J Hobbs
(74) *Attorney, Agent, or Firm* — Thomas | Horstemeyer, LLP

(57) ABSTRACT

The invention refers to a composition standardized in heterologous embryo-peptides, used as a dietary supplement and to a process for its obtainment. The composition consists of heterologous embryonic extract, standardized in embryo-peptides, maltodextrin, selenium yeast, chromium yeast, zinc chelated in embryo-peptides, pyridoxine, mixture of cationic peptides, formed by enzymatic hydrolysis of vitellus and egg white remaining after chicken embryo harvesting, with antitrypsin and endocytosis promoting activity, sodium taurocholate, expanded silicon dioxide, magnesium stearate, methylparaben and propylparaben. The process of obtainment consists of the following steps: obtaining and disintegration of biological material, diluting with sterile water, homogenization and dissociation of embryonic growth factors from their soluble receptors; embryo-peptides concentration through tangential ultrafiltration; embryo-protein denaturation and mixing of embryo-peptides with denatured proteins; obtainment of cationic peptides and their addition and of others components over the mixture embryo peptides-embryo proteins, homogenization and spray-drying of the final mixture.

7 Claims, No Drawings

(56) References Cited

FOREIGN PATENT DOCUMENTS

WO        2010130980  A2    11/2010
WO        2012070975  A1    5/2012

OTHER PUBLICATIONS

Mihăescu G., Olinescu R., Oancea F., 2005, Rom. J. Intern. Med. 43:133-9.
Mihăescu G., Olinescu R., Grigorescu A., 2006, Rom. J. Intern. Med. 44:443-53.
Schult J., Hero T., Hellhammer J., 2010, Clin. Nutr. 29:255-260.
Rotwein P., 1991, Growth Factors 5: 3-18.
Sambuy Y., De Angelis I., Ranaldi G., Scarino M.L., Stammati A., Zucco F., 2005, Cell Biol. Toxicol., 21:1-26.
International Search Report dated Jun. 26, 2014.

\* cited by examiner

COMPOSITION WITH INCREASED BIOAVAILABILITY OF ORALLY ADMINISTERED EMBRYO-PEPTIDES AND PROCESS FOR ITS OBTAINMENT

CROSS-REFERENCE TO RELATED APPLICATION

This application is the 35 U.S.C. § 371 national stage of PCT Application No. PCT/RO2013/000016, filed Sep. 17, 2013, which is herein incorporated by reference in its entirety and which also claims priority to, and the benefit of, Romanian Patent Application No. a201200665, filed Sep. 19, 2012, which is herein incorporated by reference in its entirety.

The invention refers to a composition standardized in heterologous embryo-peptides actives on human cells which, when administered orally, as a dietary supplement, for metabolism re-equilibration and regulation of metabolic disorders in human subjects, presents an increased bioavailability of the constituent embryo-peptides, and to a process for obtainment of such compositions of dietary supplement.

There are known several compositions, or processes that lead to the obtainment of such compositions, based on the extracts of heterologous embryos, of vertebrates or from the early stages of the development cycle of insects. RO Patent 74872 (published also as EP 0043842, WO102106, U.S. Pat. No. 4,405,602, GB2079602) describes a process for obtaining a biological active product from honey bees, by trituration of the drone larvae, harvested in the 10-day since the unfertilized eggs has been laid, together with the whole content of comb cells with drone brood, and homogenization and filtration of the triturate mixture to obtain a fresh product, which, when needed, could be freeze-dried to obtain a standard dehydrated product. All stages of the process are performed under aseptic conditions. The composition is claimed as having properties for: re-equilibration of the metabolism by anabolism stimulation, regulation of the menstrual cycle, increased libido and spermatogenesis in males, and improvement of the cognitive processes (C. Mateescu, Apiterapia, ed. Fiat Lux, Bucharest, 2005).

RO 107551 patent refers to a process for obtaining an extract based on embryonated eggs, and in particular of embryonated hen eggs, which is claimed to have an action of metabolic re-equilibration by stimulation of the catabolism. Similar claims relating to catabolism boosting are present also in Patent RO 107550, not only for extract of embryonated hen's eggs, but also for that of embryonated eggs of silkworm moth.

Patent application CA2197050 discloses a composition obtained from incubated shell eggs, e.g. avian eggs, and in particular hen eggs, which is useful in the prevention and treatment of cancer. A similar activity of prevention and treatment of cancers by the heterologous embryonic extracts is described by EP0929308 patent (patent published also as WO9811905; ITMI 961945; ES 2181004; DE69714856; AU3258097; AT222499). The compositions were obtained from embryonic extracts obtained from species including trout in stages of embryonic development of 5 to 20 somites, zebra fish, *Brachydanio rerio*, in stage of embryonic development of medioblastula-gastrula and vinegar flies, *Drosophila melanogaster*, in embryonic development stage of blastoderma and have been claimed to be effective not only for the treatment of tumors, but also of other pathologies controlled by p53 anti-oncogene, when administered by parenteral, oral or topical way.

U.S. Pat. No. 5,641,517 (published also as NZ254859, JPH08502041, IS4057, WO9403192, FI950369, EP0656781, DE69327585, CN1098625, CN1100545, CA2141197, AU4715093, and AT188609) describes a composition obtained by a process of extraction from fertilized incubated avian egg, dried without being prepared by the usual methods of food processing, wherein said fertilized egg is incubated to the blastodermal to protoembryonic stage. This composition, optionally together with one or more physiologically tolerable carriers or excipients, it is administered orally, in daily amounts corresponding from about 1 to about 50 g on a dry solids basis, and is claimed to have an action of increasing libido and/or serum testosterone levels.

Fertilized incubated eggs, and particularly an extract from fertilized eggs, were claimed by the International Patent Application WO2010130980 (published as US2012107411, GB2471827, EP2429537, CA2761384) as having additional physiological benefits, especially in reducing stress, such as perceived stress in an individual, and in reducing anxiety on the subjects on which it was administered, especially in chronically stressed subjects, and in normalizing the levels of cortisol in subjects chronically or non-chronically stressed and non-stressed, in response to acute stress.

US patent application US20110200737 claim a nutritional supplement composition, obtained on the basis of an extract from incubated fertilized hen eggs, intended to enhance the activity of the brain. The claimed inventive formulation use fertilized eggs incubated for 9-10 days to derive a highly potent di- and tri-peptide based amino acid based, with a high physiological activity. The rapid transport across the intestinal membrane of di- and tri-peptides is further exploited by addition of marine protein bearing high quantities of glycine, such as shark cartilage, or vegetable protein, in order to deliver a potent dose to the neuro system.

The most convenient way to administrate such compositions, based on the heterologous embryonic extracts, of vertebrates or from the early stages of the development cycle of insects, is the oral way, which is the most convenient for self-administration, allows notification as a dietary supplement and eliminates possible allergic reactions, which can occur in the case of parenteral routes of administration. The active ingredients in these composition based on heterologous embryonic extracts were considered as being amino acids, vitamins and pre-hormones. (Patent RO74872, U.S. Pat. No. 5,641,517) or di- and tri-peptides (US Patent Application US20110200737). But such ingredients are not highly specific to embryonic extracts. In the quantities of order of grams from the heterologous embryonic extracts, administered as a dietary supplement, amino acids, (pre) hormones and/or vitamins are not in doses high enough to trigger the physiological responses which are claimed by different patents that protect compositions of heterologous embryonic extracts and/or corresponding processes for their obtainment. Embryo-peptides of larger dimensions, and especially those having growth factors activities, that are specific present on vertebrate embryos or in the early stages of the development cycle of the insect, were regarded as being the active ingredients of these embryonic extracts, especially embryonic extracts form chicken embryos/incubated fertilized hens eggs, which are explaining more convincingly physiological effects (Mihăescu G., Olinescu R., Oancea F., 2005, *Rom. J. Intern. Med.* 43:133-9; Mihăescu G., Olinescu R., Grigorescu A., 2006, *Rom. J. Intern. Med.* 44:443-53; Schult J., Hero T., Hellhammer J., 2010, *Clin. Nutr.* 29:255-260). Such growth factors, which are specifically present in embryonic extracts, are very highly conserved during evolution (e.g., insulin-like growth factors are members of the superfamily of insulin, being highly conserved during evolution, according to the review of Rotwein P., 1991, Growth Factors 5: 3-18).

U.S. Pat. No. 4,908,206 discloses a new process for obtainment of an extract from organs of embryos of mammals, which is free of non-polar constituents and constituents having a high molecular weight. The extract is prepared according to a new process of extraction, in which the first stage extraction of finely divided embryonic mammalian organs is carried out by treatment with a mixture of water and a water soluble organic solvent, or with a mixture of organic solvents water soluble. In this mixture, used for the first stage extraction, mixture of organic solvents soluble in water accounts at least 70 volume percent of said organic solvent in the total volume of the mixture of extraction and has a neutral pH value, in order to avoid degradation of proteins with high molecular weight. Extract recovered in accordance with the procedure contains only those polar constituents that have a molecular mass of less than 5 kDa, which are present in fresh bodies of mammalian embryos, and does not contain compounds that are derived from the degradation of protein structures. The composition obtained by the method described by U.S. Pat. No. 4,908,206 is not intended for oral administration, but for topical use, as the treatment of acne vulgaris. The limit of 5 kDa molecular mass is below the value of some of the peptide growth factors present in embryonic extracts (IGF-1 has a molecular weight of 7649 Da, calculated according to Rinderknecht E., Humbel, R. E., 1978, *J. Biol. Chem.* 253: 2769-277), thus these growth factors are excluded from preparations obtained by the process disclosed by U.S. Pat. No. 4,908, 206.

RO Patent 119509 describes a composition based on avian embryo, enriched in peptides with molecular weight lower than 10 kDa by a batch gel-chromatographic process, which contains also enhancers of intestinal absorption of peptides (sodium taurocholate) and trypsin inhibitors. This composition is designed to assure a higher resistance of embryonic peptides to degradation by proteases in the digestive system/ duodenum and for better absorption of embryo-peptides through the intestinal barrier.

Despite the presence of trypsin inhibitors and of promoter of intestinal absorption of peptides, composition presented by RO Patent 119509 continues to show a high variability of physiological responses on the human subjects when is orally administrated. One of the reasons is due to the fact that the biologically active embryo-peptides from the initial embryonic extract, and especially those with growth factors activities, are linked to specific ligands, cell receptors or soluble receptors—e.g. Insulin-like growth factor-binding protein, IGFBPs, for IGFs. These macromolecular complexes structures, in which growth factors are related to their specific ligands with a high affinity, have a molecular mass greater than 10 kDa, cannot be enriched in the composition carried out by the process disclosed by RO Patent 119509 and finally determine a variable absorption through the intestinal barrier, being responsible for the high variability of physiological responses of the human subjects in the case of oral administration. The process of enrichment through batch gel-chromatography causes a dilution of the extracts, the removal of excess water causing extra cost, so it is necessary an improved process, which should assure a higher yield on enrichment in embryo-peptides, with a lower dilution of the extract.

It is necessary the introduction on the processes for obtainment of the embryonic extracts standardized in embryo-peptide of a dissociation step, of the growth factors from their complexes with their receptors, and especially from their soluble receptors. Insulin-like growth factors, which have been demonstrated to be one of the main active ingredients of preparations with embryo-peptides (Mihăescu G., Olinescu R., Grigorescu A., 2006, *Rom J Intern Med.* 44:443-53) are dissociated from their soluble receptors IGFB-5, present in significant amounts in the chicken embryo, by $Zn^{2+}$ ions (McCusker M. H., Novafoski J., 2004, *J. Endocrin.* 180: 227-246). But $Zn^{2+}$ ions should be introduced into the exact stoichiometric amount required for dissociation of IGF-IGFB, avoiding the excess ions which may result in re-association of other embryo-peptides with physiological activity. Using insoluble zinc compounds, such as zinc oxide or zinc carbonate, it could avoid excess ions $Zn^{2+}$. The chelating reaction IGF-$Zn^{2+}$ displaces the equilibrium solubility product of the insoluble zinc compounds, especially of zinc carbonate, but the formation of peptide chelates from insoluble compounds, salts, oxides/ hydroxides of metals requires large amounts of water and a long period for the chemical reaction, as is described in the process that is protected by U.S. Pat. No. 4,830,716. Longer reaction time and the need to spray drying of a diluted suspension involve a high risk of microbial contamination and higher manufacturing costs. It is therefore necessary to develop a step in the process of obtainment of embryopeptide compositions, with increased bioavailability when are orally administrated, which shall be carry out in concentrated solutions and which shall assure a shorter time for the formation of chelates with peptides/growth factors, and for the dissociation of these growth factors from their soluble receptors, using insoluble compounds of zinc as the source assuring the exact $Zn^{2+}$ ions amount required by reaction stoichiometry. It is also necessary to develop a process that allows the inclusion of the peptidic growth factors from the embryonic extracts in compositions which, when are orally administered and are arriving in intestine, are stimulating the endocytosis, as an effective way to penetrate the intestinal barrier. Such compositions with increased bioavailability due to endocytosis stimulation should reduce the variability of physiological responses, promoting reproducible metabolic re-equilibration and regulation of metabolic disorders in human subjects, to which are administered for several weeks.

The invention aims to solve the technical problems described above by providing an embryo-peptides based composition and a process for obtainment of this from vertebrate embryos extract or from the early stages of the development cycle of the insects, which, when is orally administrated, as a dietary supplement, for metabolic re-equilibration and regulation of metabolic disorders, presents an increased bioavailability of constituent embryo-peptides. Enrichment in embryo-peptides, with cytostimulating activity and cytoprotective activity on human cells, is achieved without significant dilution of the extract. The invention also has the aim to introduce a step of dissociation of peptide growth factors in the process of obtainment, in order to allow concentration of the growth factors after dissociation from their soluble receptors using $Zn^{2+}$ ions provided as the exact stoichiometry quantity required, and which is carried out in concentrated solutions and in short time. Under another aspect the invention provides a process which lead to composition of embryo-peptides with increased bioavailability, that are absorbed through the intestinal barrier reequilibrating the metabolism by adaptive regulation mechanisms, triggered by neuro-endocrine axis, hypothalamic-pituitary-adrenal.

Composition with increased bioavailability of orally administered embryo-peptides according to the invention is the following: 20 parts of heterologous embryonic extract, standardized in embryo-peptides, 80 parts of maltodextrin, 2 parts selenium yeast containing 750 mg Se per kg, 1.5 part chromium yeast containing 900 mg Cr per kg, 0.2 parts of zinc chelated in embryo-peptides, 0.2 parts vitamin B6, pyridoxine, 0.5 parts of cationic peptides mixture, formed by enzymatic hydrolysis, of the vitellus and of the egg white, remaining after harvesting the chickens embryos, which have a specific antitrypsin activity, of 980±53.3 BAEE units per mg of peptide, and intestinal epithelium endocytosis promoting activity, 0.5 parts of sodium taurocholate, 0.01 . . . 0.015 parts of expanded silicon dioxide, 0.01 . . . 0.015 parts of magnesium stearate, 0.01 . . . 0.015 parts of methylparaben and 0.005 parts . . . 0.010 parts of propylparaben, parts being expressed in units of weights.

The process for obtainment of the compositions with increased bioavailability of orally administered embryo-peptides according to the invention includes the following steps: obtainment of the biological material with a very low biological contamination, by aseptic harvesting of chicken embryos, together with chorioallantoic membranes, from eggs fertilized and incubated for 10 days, or disinfection of the silkworm mouth non-diapause eggs, or aseptic harvesting of the drone brood/male larvae of *Apis melifera*, at 10 days after haploid eggs laying, more exactly of larvae old of 7 days; disintegration of the biological material by using a colloidal mill and determination of the dry matter content into the extract; dilution of 10 parts of disintegrated embryos, expressed as dry matter, with 90 parts of sterile distilled water; homogenization of the diluted disintegrated embryos with a piston homogenizer at high pressure, two cycles at 50 MPa; mixing 100 parts of the resulting suspension with 1.25 parts zinc carbonate and ultrasonication for 25 min at 500 W, to assure the dissociation of growth factors and their receptors; removal of excess zinc carbonate and of cellular debris by centrifugation; embryo-peptides from supernatant concentration by tangential ultrafiltration through a 10 kDa membrane; denaturation of the protein, from the ultrafiltration retentate, which have a molecular weight >10 kDa, by heating to 85° C. for 25 min; mixing of ultrafiltration dialysate which contain embryo-peptides <10 kDa, with ultrafiltration retentate with denatured protein >10 kDa, in ratio 1 part peptides to 9 parts protein in the case of chickens embryos, and 1 part peptides to 4 parts protein in the case of biological material originating from the early stages of insect development, and homogenization on a piston homogenizer, 1 cycle to 30 MPa; enzymatic hydrolysis with endo-protease of vitellus and egg white remaining after harvesting the chickens embryos, in a ratio of 2 parts endo-protease per 100 parts of vitellus and egg white remaining after harvesting the chickens embryos, followed by tangential ultrafiltration of the peptides with a molecular weight of less than 10 kDa, absorption from ultrafiltrate dialysate of the formed cationic peptides, on a cation exchange resin, elution of the cationic peptides from the ion exchange resin and determination of peptide concentration with Folin-Ciocâlteu reagent; adding over the specific amount of eluate containing 0.5 parts of cationic peptides, which have a specific antitrypsin activity, of 980±53.3 BAEE units per mg of peptide, and intestinal epithelium endocytosis promoting activity, of 80 parts maltodextrin, 2 parts selenium yeast containing 750 mg Se per kg, 1.5 parts chromium yeast containing 900 mg Cr per kg, 0.2 parts vitamin B6, pyridoxine, 0.5 parts sodium taurocholate, 0.01 . . . 0.015 parts expanded silicon dioxide, 0.01 . . . 0.015 parts magnesium stearate, 0.01 . . . 0.015 parts methylparaben and 0.005 parts . . . 0.010 parts propylparaben and mixing with 20 parts of embryo-peptide-denatured embryonic protein mixture containing also 0.2 parts of zinc chelated in embryo-peptides; homogenization of the resulted mixture by using a piston homogenizer at high pressure, 2 cycles at 35 MPa; spray-drying of the final mixture, at max. 10 kg/h, using a centrifugal atomizer operated at 20,000 rpm, at an air inlet temperature of 140 . . . 150° C. and an air outlet temperature of 80 . . . 85° C.

Composition with increased bioavailability of orally administered embryo-peptides in accordance to the invention, when is administrated as dietary supplement in dose of 2 capsules one hour after breakfast and 2 capsules one hour after lunch, for a period of a minimum 60 days, re-equilibrate the metabolism, increases the level of androgens in young men, normalize cortisol level, decreased total triglyceride, total cholesterol and its low-density lipoprotein fraction and increased the heavy density lipoprotein fraction on human subjects of third age.

By application of the invention results the following advantages:
assure an increased bioavailability of peptides active ingredients, as a result of endocytosis stimulation due to the presence of cell penetrating cationic peptides and of taurocholate, and of absorption through endocytosis of the embryo-peptides included inside of the structures formed together with degraded proteins >10 kDa, which have emulsifying properties;
concentration of embryo-peptide without further dilution of the peptides from the extract;
provide the exact quantity of $Zn^{2+}$ ions required by stoichiometry of reaction, in the step of dissociation of growth factors, prior to the step of embryo-peptides separation through ultrafiltration;
reduces the quantity of by-products and of purchasing costs of formulation additives, acting as emulsifying agents or as cell penetrating peptides, by using the by-products, to produce emulsifying agents through the degradation of proteins >10 kDa, from ultrafiltration retentate, and, respectively, to produce cell penetrating peptides by enzymatic hydrolysis and further separation on cationites, from the remaining vitellus and egg white;
assure an increased productivity;
reduced the loss on active substances, by thermo-degradation and thermo-oxidation;
promote the obtainment of a product with good flowing characteristics;
promote the formation of a product with increased physico-chemical and microbiological stability, of which the validity term is higher than 2 years.
assure the possibility to adapt to various sources of heterologous embryos.

This invention is illustrated by the following examples

EXAMPLE 1

Embryos from fertilized and embryonated hens eggs are aseptically harvested and then are disintegrates into a colloidal mill (Colloid Mill Karl Schell KS 030-F10-150), until the formation of a uniform particle homogenate. In the homogenate is determined the dry matter, by refractometry, and then the homogenate is mixed with water, 10 parts embryonic homogenate with 90 . . . 95 parts of sterile distilled water, and re-homogenized by using a piston homogenizer (GEA Niro Soavi Arriete NS2006), two cycles at 50 MPa. The resulting suspension is mixed with 1.25 parts of zinc carbonate and is ultrasonicated for 25 min to 500 W (with Hielscher UIP 100hd equipment), to assure the dissociation of growth factors from their receptors, to which form complexes that would remain in the retentate in case of ultrafiltration. Excess of zinc carbonate and of others insoluble residues, such as for example cell debris, are removed by centrifugation (Alfa Laval LAPX 404, 20 liters per min, 5000 rpm, CA. 5500 g). The supernatant is then tangentially ultrafiltrated through a 10 kDa membrane, using as equipment Millipore Pelicon 2 Maxi Cassete Biomax 10, 2.5 m². In ultrafiltration retentate the pH is adjusted to pH 7.0 with 1 M sodium hydroxide and solution of protein with molecular weight >10 kDa is heated in a jacketed reactor, for 25 min at 85° C., in order to assure the denaturation of non-polar links and of disulfide bridges, and thus to improve the emulsifying capacity of these embryo-protein. Denatured proteins are mixed with peptides containing ultrafiltrate, in a ratio of 1 part peptides to 9 part protein, peptide and protein content being determined by Lowry method using the Folin reagent Ciocâlteu (Lowry O. H., Rosebrough N. J., Farr A. L., Randall R. J., 1951, *J. Biol. Chem.* 193: 265-75). The mixture is homogenized one cycle on a piston homogenizer at 30 MPa.

Vitellus and the rest of the egg white remaining after harvesting chicken embryos are places in a reaction vessel and are treated with Alcalase AF 2.4 L (Novozyme), endo-protease from *Bacillus licheniformis*, with subtilisin/serine-endopeptidaze as the main component, with a specific enzymatic activity of 1.5 units Anson (AU) per gram, (one AU is the amount of enzyme which digests hemoglobin in standard conditions with an initial rate that produces in a minute a quantity of reaction products soluble in trichloroacetic acid forming the same color with the Folin reagent-Ciocâlteu as a milliequivalent of tyrosine), in a ratio of 2 parts endo-protease to 100 parts vitellus and egg white. The mixture is heated to 50° C., is maintained for 30 min and then is pumped on a tangential Millipore ultrafiltration equipment Millipore Pelicon 2 Maxi Cassete Biomax 10, 2.5 m², equipped with 10 kDa membrane, for 15 min. Retentate is returned to the reaction vessel and the dialysate is received into a vessel, where is treated on stirring with Bio Rex 70 resin, cation exchanger, 200-400 mesh, washed with 1 N HCl and then with distilled water, in a proportion of 5 parts resin per 100 parts dialysate. The cycle of enzymatic hydrolysis/ultrafiltration is repeated 10 times, adding ion exchange resin in the vessel where the dialysate is received, in order to maintain the proportion of 5 parts resin per 100 parts dialysate. After completing the enzymatic hydrolysis cycles the dialysate is kept with the resin for 4 hours. Resin is filtered, rinse abundantly with distilled water and is packed in a column from which are eluted the peptides, with a gradient 0.2 . . . 2 M NaCl, and at elution rate of 3.5 ml per min. From the eluate the excess salt is removed through overnight dialysis. On dialysate is determined the peptide content with Folin-Ciocâlteu reagent. In one volume of dialysate containing 0.5 parts of cationic peptides, which have a specific antitrypsin activity, of 980±53.3 BAEE units per mg of peptide, and intestinal epithelium endocytosis promoting activity, are added 80 parts of parts maltodextrin, 2 parts of selenium yeast containing 750 mg Se per kg, 1.5 part of chromium yeast containing 900 mg Cr per kg, 0.2 parts of vitamin B6, pyridoxine, 0.5 parts of sodium taurocholate, 0.01 . . . 0.015 parts of expanded silicon dioxide, 0.01 . . . 0.015 parts of magnesium stearate, 0.01 . . . 0.015 parts of methylparaben and 0.005 parts . . . 0.010 parts of propylparaben and are mixed with 20 parts of embryo-peptide-denatured embryonic protein mixture containing also 0.2 parts of zinc chelated in embryo-peptides. The above resulted mixture is homogenized on a piston homogenizer at high pressure, 2 cycles at 35 MPa and then the final mixture is spray-drayed, at max. 10 kg/h, using a centrifugal atomizer operated at 20,000 rpm, at an air inlet temperature of 140 . . . 150° C. and an air outlet temperature of 80 . . . 85° C.

Embryo-peptides separated by tangential ultrafiltration, with a molecular weight of less than 10 kDa, were tested regarding their effect of human cells grown in vitro. Cell line used was the diploidic human cell line ICP-INCDMI 23 (INCDMI "Cantacuzino", Gaicu, D. Petrasincu, S. Nachtigal, I. Stoian, 1997, Developm. Biol. Standardiz., 37:19-21). Cell line which was used is a normal human cell line, genetically stable in time in vitro for the entire lifespan. The cells were maintained in the laboratory by serial multiplication, with a dispersion rate 1:2, in Eagle BME growth media supplemented with 10% calf serum.

The tests were carried out by growing the cells in 2 ml Barski tubes. Culture medium used for the testing of embryo-peptides extracted from embryos of chickens was Eagle BME supplemented by a half reduced fetal bovine serum quantity (5% instead of 10%), which was supplemented with 1% embryo-peptides from chicken embryo, concentrated in the ultrafiltrate dialysate. The results were compared to a standard, represented by Eagle BME supplemented 10% fetal bovine serum, and a control, the fibroblasts grown on Eagle BME supplemented by supplemented by a half reduced fetal bovine serum quantity.

In vitro cell proliferation assessment was performed by measuring and recording cell density at intervals of 24 hours, over a cycle of multiplication (96 hours), at 37° C., in an atmosphere humidified with excess carbon dioxide (5% $CO_2$, 95% air). The dynamics of cell growth in vitro was recorded by reporting cellular density (cells/cm²) to the corresponding interval in hours. Counting of cells was done after sample preparation, by detachment of cells with trypsin, cell recovery in a known volume of growth medium and specific staining (tripan blue 0.4%). The technique used allow also a cell mortality estimation (as a percent; dye exclusion assay). All reagents used were provided by Sigma-Aldrich (Sigma-Aldrich, St. Louis, Mo., USA). The results are presented in table 1.

TABLE 1

The effect of embryo-peptides from embryonic chicken extract, concentrated in the ultrafiltrate dialysate on the growth and mortality of fibroblast cell ICP-23 ($23^{th}$ passage in vitro).

| Experimental treatment | Cell number ($\times 10^4/cm^2$) | | The mortality, (%) | |
| --- | --- | --- | --- | --- |
| | 72 h | 96 h | 72 h | 96 h |
| Standard (BME with Eagle 10% fetal bovine serum) | 12.43a | 13.25c | 4.20e | 5.11g |
| Eagle BME with 5% fetal bovine serum + 1% embryo-peptides | 12.18a | 13.05c | 1.81f | 2.68h |
| Control (Eagle BME with 5% fetal bovine serum) | 10.32b | 9.73d | 3.92e | 4.64gh |

* Values followed by the same letter does not differ significantly for $P < 0.05\%$ Embryo-peptides from chicken embryo concentrated in ultrafiltrate dialysate have shown a cytostimulating and cytoprotective action on human fibroblasts (ICP-line $23^{th}$ passage in vitro). After 96 hours cell number was higher with more than one-third comparing to control (Eagle BME with 5% fetal bovine serum, $9.73 \times 10^4$ cells/cm$^2$, Eagle BME with 5% fetal bovine serum+1% embryo-peptide–$13.05.10^4$ cells/cm$^2$). At the same time at 96 hours mortality of treated cells with embryo-peptides (2.68%) is nearly 50% of the mortality on standard treatment, 10% fetal bovine serum (5.11%).

The mixture of cationic peptides obtained from vitellus and egg white remaining after harvesting chicken embryos have been tested for activity of trypsin inhibition and stimulation of endocytosis.

Inhibition of trypsin activity was determined using BAEE as substrate, through continuous monitoring of the UV absorption at 254 nm. In a quartz cuvette with optical path length of 1 cm were introduced 2 ml of mixture 63 mM sodium phosphate, 0.23 mM N-α-benzoyl-L-arginine ethyl ester of (BAEE-N-α-Benzoyl-L-arginine ethyl ester hydrochloride), 0.002 mM hydrochloric acid, 0.005 mg trypsin and 0.005 mg mixture of cationic peptides. The mixture was homogenized by inverting quartz cuvette and was determined the increase of absorbance in UV at 254 nm in a spectrophotometer UV-VIS the Pharo Spectroquant Merck Millipore 300. The experiment was done with a control for reagents, $M_R$, without addition of trypsin and mixture of cationic peptides, and a standard $M_T$, on which was only added trypsin. All reagents used were provided by Sigma-Aldrich (Sigma-Aldrich, St. Louis, Mo., USA). Determinations were performed in triplicate, and the activity of trypsin inhibition was calculated according to the formula:

Activity of trypsin inhibition=$(OD_{253nm}/\min M_T - DO_{253nm}/\min M_R) - (OD_{253nm}P - OD_{253nm}M_R)*200$ where:

$DO_{253nm}/\min M_T$ is variances in the UV absorbance at 253 nm of MT standard, wherein only trypsin were added;

$DO_{253nmR}/\min M_R$ is the variance in the UV absorbance at 253 nm of the of reagents control $M_R$, wherein was only added reagents;

$DO_{253nm}/\min P$ is variance in the UV absorbance at 253 nm of the sample with trypsin and trypsin inhibitor form the mixture of cationic peptides;

200 is the correction factor for the activity for one mg of trypsin/mixture of cationic peptides containing trypsin inhibitor.

A trypsin/antitrypsin BAEE activity is defined as the enzymatic hydrolytic activity of the peptides specific for trypsin, which determines in a minute a variation of optical density at 253 nm of 0.001, when the substrate used is N-α-benzoyl-L-arginine ethyl ester (BAEE). The mixture of cationic peptides obtained from vitellus and the egg white remaining after harvesting chicken embryos has shown an activity of 980±53.3 BAEE per mg.

In order to determine the influence of cationic peptides obtained from vitellus and egg white remaining after harvesting of embryos it was used the monolayer technique of Caco-2 cells, a model widely used for intestinal barrier (Sambuy Y., De Angelis I., Ranaldi G., Scarino M. L., Stammati A., Zucco F., 2005, *Cell Biol. Toxicol.*, 21:1-26). Caco-2 cells (American Type Culture Collection, ATCC, Manassas, Va., USA) were maintained in the modified Eagle medium after Dulbecco, pH 7.4, supplemented with 10% fetal bovine serum, 2 mM L-glutamine, 1% solution of essential amino acids and solution of 0.1% penicillin-streptomycin, at 37° C., in an atmosphere humidified and with excess carbon dioxide (5% $CO_2$, 95% air). The cells were grown in standard conditions until the confluence of 60 . . . 70%. Cells in the 30 . . . 40 passages were used in all experiments. Caco-2 cells were inoculated into a 12 wells plates Transwell® (Costar®, Corning, Corning, N.Y., USA), with polycarbonate membrane filters for cell cultures (pore size 3 μm), at a density of inoculation of $2 \times 10^4$ cells/cm$^2$. The culture medium was added to both apical and basolateral chamber. The culture medium was changed every day. The cells were allowed to differentiate for 20 days after inoculation, with monitoring of trans-epithelial resistance (TEER—TransEpithelial Electrical Resistance), by using of an EVOM digital voltohmmeter (World Precision Instruments, Sarasota, Fla., USA). On the monolayer of Caco-2 cells was determined the influence of the mixture of cationic peptides obtained from remaining vitellus and egg white on the transport of dextran marked with fluorescein FD-4 (average molecular weight 3 . . . 5 kDa). Before transport experiments the cells were washed twice with sterile PBS and balanced for an hour with Hank's buffered saline solution (HBSS, Hank's Buffered Salt Solution). After washing the culture medium the cells were treated with cationic peptides, solution 1 mg/ml final concentration in HBSS, on the apical chamber for 2 hours. In the control wells was only HBSS. After 2 hours of treatment, the cells were washed with sterile PBS and a solution of FD-4 was added to the apical side of cell monolayer, in a final concentration of 1 mg/ml. From the basolateral side were taken samples of 1 ml at 60, 120, 180 and 240 min replacing the sample withdrawn with a sterile HBSS solution. FD-4 concentration in samples taken from the basolateral side was determined by using a spectrofluorometer Jasco FP6500 (Jasco, Easton, Md., US) at an excitation wavelength of 400 nm and at an emission wavelength of 550 nm. The results were expressed as cumulative transport depending on time. All experiments were conducted in triplicate at 37° C. All reagents used were provided by Sigma-Aldrich (Sigma-Aldrich, St. Louis, Mo., USA).

The apparent permeability coefficient was calculated by the following formula:

$P_a = (\delta C/\delta t) \times (1/A \times C_o)$ where:

$P_a$ is apparent permeability coefficient (cm/s)

$\delta C/\delta t$ is the rate of appearance of FD-4 in basolateral chamber (mg/s)

A is the area of monolayer of CaCo-2 cells $C_o$ is the initial concentration of FD-4 in the apical chamber.

The rate of apparition of FD-4 was calculated as the slope of the linear function of permeation depending on time. Stimulating the absorption ratio (R) was determined from the values $P_a$ according to the following formula:

$R = P_a(\text{sample})/P_a(\text{untreated control})$

The results are presented in table 2. These results demonstrate that the cationic peptides produced by enzymatic hydrolysis of remaining vitellus and egg white stimulates transport of FD-4 (average molecular weight 3 . . . 5 kDa), stimulating the absorption Ratio R=14.33, the most probably by stimulating endocytosis after the non-specific interaction with the polyanionic mucus of the extracellular matrix.

TABLE 2

Effect of cationic peptides produced by enzymatic hydrolysis of vitellus and egg white remaining after harvesting chicken embryo, on transport of FD-4 through the monolayer of Caco-2 cells.

| Experimental treatment | FD-4 cumulated transport at 4 hours (μg) | Apparent permeability coefficient $P_a$ ($10^{-6}$ cm/s) | Stimulation of the absorption ratio R |
|---|---|---|---|
| Control(HBSS) | 2.23 ± 0.8 | 0.12 | 1.00 |
| Cationic peptides | 27.86 ± 2.2 | 1.72 | 14.33 |

Selenium yeast used in this example is obtained by the following process. The following culture medium for yeasts (*Saccharomyces cerevisiae, Candida utilis*) is realized: 30 ... 32 parts glucose, 0.7 ... 0.8 parts magnesium chloride ($MgCl_2.6H_2O$), 0.4 ... 0.5 parts disodium phosphate ($Na_2HPO_4$), 0.6 ... 0.75 part monopotassium phosphate ($KH_2PO_4$), 5 ... 6 parts of selenium yeast plasmolyzate, 1.5 ... 2 parts of derivative of thiazolidine-4-carboxylic acid. Selenium yeast plasmolyzate is obtained as follows: 500 parts of baker's yeast (STAS 985-79, 26% dry matter) it is emulsified with 2400 ... 2500 parts of water, it is maintained for 30 min at 70 ... 75° C., it is sterilized 20 min at 105° C., it is cooled at 30 ... 35° C., it is treated with 0.08 ... 01 parts of sodium metabisulphite ($Na_2S_2O_5$) and after 30 min. are added 0.16 ... 0.18 parts of sodium selenite ($Na_2SeO_3$. 5 $H_2O$). The mixture it is homogenized at medium pressure (150 ... 200 bar) and it is spray-dried using a centrifugal atomizer (air inlet temperature of 140 ... 150° C. and an air outlet temperature of 80 ... 85° C.). The derivative of thiazolidine-4-carboxylic acid is obtained as follows: ribose 1.5 parts of ribose, 1.5 parts of cysteine hydrochloride and 1.1 parts of calcium carbonate ($CaCO_3$) are dissolved in 30 parts water to 40 ... 50° C., then are maintained for 24 hours at 37° C.; the excess calcium carbonate is filtered, filtrate is concentrated under vacuum until the 5 ... 6 parts and it is precipitated with ethanol. The precipitate is recovered with a mixture of acetone:ethanol 40:60 and crystallized by using a boiling water bath.

Culture medium is sterilized by filtration and then is passed to a thermal sterilized bio-reactor, cooled to 30 ... 35° C. After reaching the cultivating temperature of 32 ... 35° C. the medium is inoculated with 10 ... 15 parts of pure yeast culture suspension, containing 14 ... 15 g yeast/l, obtained by cultivation in flasks, in accordance with the usual procedures, on a culturing media identical to that described above. The yeast are grown 10 ... 12 hours in aerobiotic condition, at a temperature 32 ... 35° C., pH of 6.4 ... 6.8 u pH and at a rate of aeration of 1.2 ... 1.4 liters per liter of culture media and per minute. After the end of the period of cultivation on aerobic condition the culture medium is flushed for 10 ... 15 min with pure nitrogen, with a rate of 1.4 ... 1.6 liter of nitrogen per liter of medium and per minute and then the yeast is cultivated in anaerobiotic conditions, for 10 ... 12 hours at a temperature of 25 ... 28° C. and at a pH of 5.6 ... 6.0 u. pH. At the end of the period of cultivation in anaerobiotic conditions it is started the aeration, at the rate of 0.1 liters of air per liter of medium and per min, which increases till reaching the initial rate of 1.2 ... 1.4 liters of air per liter of culture medium and per minute. The growth on aerobiotic condition is continued at 32 ... 35° C. and at a pH of 6, 4 ... 6.8 u pH for 10 ... 12 hours. Upon reaching level of 16 ... 18 g yeast per liter of medium, the yeast biomass is separated by continuous centrifugation to 8000 ... 10000 g, the resulted yeast milk is subjected to the plasmolysis by heat shock, for 30 ... 35 min at 70 ... 75° C. Yeast plasmolyzate is sterilized for 20 minutes at 105° C., cooled to 60 ... 65° C., homogenized at medium pressure (100 ... 200 bar) and it is spray-dried using a centrifugal atomizer (air inlet temperature of 140 ... 150° C. and an air outlet temperature of 80 ... 85° C.).

Chromium yeast used in this example is obtained according to the following procedure. 500 parts of baker's yeast (STAS 985-79, 26% dry weight) is emulsified with 2400 ... 2500 parts of water, for 30 min at 70-75° C., it is sterilized for 20 min at 105° C., cooled at 30 ... 35° C., and after 30 min are added 0.12 ... 0.14 parts of chromium chloride. The mixture is homogenized at medium pressure (150 ... 200 bar) and centrifuged 20 min to 6000 g. The sediment is discharged and the supernatant is spray-dried using a centrifugal atomizer (air inlet temperature of max. 150° C. and an air outlet temperature of max. 85° C.).

Any other forms of selenium yeast or chromium can be used.

Powder containing embryo-peptides with high bioavailability of oral administration, resulting from this example, contains active principles from the chicken embryos with an oligo-peptide structure, whose physiological action is amplified by micro- and oligoelements (Zn, Cr, Se), chelated in compounds with high bioavailability.

Product obtained by applying this example has the following characteristics:
appearance: fine powder, corresponding to the provisions of *International Pharmacopoeia*;
color: white-yellowish to pale green;
smell: characteristic;
taste: specific, with a slight sweet taste;
humidity (loss by drying at 105° C. for 4 hours): max. 6%;
protein content (as total nitrogen×6.25): 10%
peptides (acid-soluble, with Folin-Ciocâlteu reagent): 10 mg/g;
total selenium content: min. 15 mg/kg;
total chromium content: min. 12.5 mg/kg;
total zinc content: min. 0.19%
pyridoxine content: min. 0.19%

Concentrated protein powder enriched in peptides obtained by applying this example is processed into forms of dietary supplements with gastro-resistant unit doses (e.g. operculated capsules), for oral administration.

Example of invention embodiments can be done also with other avian embryos (turkeys, duck, quail, etc.), collected the day before of half of their complete embryonic development cycle until hatching.

EXAMPLE 2

Non-diapause eggs of silkworm moth, *Bombyx mori*, embryonated for 7 days, were disinfected by repeated washing, 3 times with a solution with 200 ppm of active chlorine (prepared by diluting 0.5 ml of sodium hypochlorite solution into 0.5 liters of water) for 1 min, followed by rinsing with sterile deionized water for 3 min. The washing ratio was 1 part embryonated silkworm moth eggs at 10 parts bleach solution active. Disinfected eggs of silkworm mouth have been subjected to the process of obtaining standardized composition in embryo-heterologous peptides, as described in example 1, with the only difference that the step of mixing of embryonic embryo-peptides with mass <10 kDa with embryo-degraded proteins with masses >10 kDa, it is in the ratio of 1 part embryo-peptides to 4 parts embryo-proteins.

Addition of a higher amounts of embryo-peptides derived from embryonated silkworm moth eggs, is determined by their lower cytostimulating and cyto-protective action, as it results from the test effect on human fibroblast cell line ICP-23, presented below.

The tests were conducted as they were presented in example 1, by growing the cells in 2 ml Barski tubes. Culture medium used for the testing of embryo-derived peptides from embryonated silkworm mouth eggs was BME Eagle, supplemented with a quantity of fetal bovine serum reduced to half (5%), which was supplemented also with 1% embryo-peptides from embryonated silkworm eggs, concentrated in ultrafiltrate dialysate.

TABLE 3

Effect of embryo-peptides from embryonated silkworm eggs, concentrated in ultrafiltrate dialysate, on the growth and mortality of fibroblast cell ICP-23 ($23^{th}$ passage in vitro).

| Experimental treatment | Cell number ($x^4$ at $10/cm^2$) | | Cell mortality (%) | |
|---|---|---|---|---|
| | 72 h | 96 h | 72 h | 96 h |
| Standard (BME with Eagle 10% fetal bovine serum) | 12.28a | 13.40c | 4.30e | 5.24g |
| Eagle BME with 5% fetal bovine serum + 1% embryo-peptides | 11.58ab | 12.55cd | 3.35f | 3.82h |
| Control (Eagle BME with 5% fetal bovine serum) | 10.12b | 10.89d | 3.94e | 4.52gh |

* Values followed by the same letter does not differ significantly for $P < 0.05\%$ The results were compared to a standard, represented by Eagle BME supplemented 10% fetal bovine serum, and a control, the fibroblasts grown on Eagle BME supplemented by a quantity reduced to half of fetal bovine serum (5%). The results are presented in table 3.

Embryo-peptides from embryonated silkworm moth eggs, concentrated in ultrafiltrate dialysate shown a cytostimulating and cytoprotective action on human fibroblasts (ICP-line passage in vitro23) less pronounced than that of embryo-peptides from chicken embryo. After 96 hours cell number is higher with approx. 15% (Eagle BME with 5% fetal bovine serum $10.12 \times 10^4$ cells/$cm^2$, Eagle BME with 5% fetal bovine serum+1% embryo-peptides, $11.58 \times 10^4$ cells/$cm^2$). At the same time, at 96 hours, the mortality of treated cells with embryo-peptides (3.82%) is 72.9% of the mortality which is present on the standard with 10% fetal bovine serum (5.24%).

This lower biological activity on human fibroblasts of embryo-peptides from embryonated silkworm moth eggs, compared to that of the embryo-peptides from the extract chicken embryo is explicable considering the evolutionary distance. To compensate for this difference on biological activity in the process of obtaining embryonic extracts based on composition of embryonated silkworm moth eggs has proceeded to doubling the concentration of the embryo-peptides with molecular weight >10 kDa, concentrated in the ultrafiltrate dialysate.

Product obtained by applying this example has the following characteristics:
  appearance: fine powder, corresponding to the provisions of *International Pharmacopoeia;*
  color: white-yellowish to pale green;
  smell: characteristic;
  taste: specific, with a slight sweet taste;
  humidity (loss by drying at 105° C. for 4 hours): max. 6%;
  protein content (as total nitrogen×6.25): 10%
  peptides (acid-soluble, with Folin-Ciocâlteu reagent): 20 mg/g;
  total selenium content: min. 15 mg/kg;
  total chromium content: min. 12.5 mg/kg;
  total zinc content: min. 0.19%
  pyridoxine content: min. 0.19%

EXAMPLE 3

Drone larvae were collected aseptically from the honey-comb cells, at 10 days after haploid eggs laying, when larvae age are of 7 days. The larvae harvested in aseptic conditions have been subjected to the process of obtaining standardized composition in embryo-heterologous peptides, as described in example 1, with the only difference that the step of mixing of embryonic embryo-peptides with mass <10 kDa with embryo-degraded proteins with masses >10 kDa, it is in the ratio of 1 part embryo-peptides to 4 parts embryo-proteins.

Addition of a higher amounts of embryo-peptides derived from drone larvae, is determined by their lower cytostimulating and cyto-protective action, as it results from the test effect on human fibroblast cell line ICP-23, presented below.

The tests were conducted as they were presented in example 1, by growing the cells in 2 ml Barski tubes. Culture medium used for the testing of embryo-derived peptides from drone larvae was BME Eagle, supplemented with a quantity of fetal bovine serum reduced to half (5%), which was also supplemented with 1% embryo-peptides from drone larvae, concentrated in ultrafiltrate dialysate. The results were compared to a standard, represented by Eagle BME supplemented 10% fetal bovine serum, and a control, the fibroblasts grown on Eagle BME supplemented by a quantity reduced to half of fetal bovine serum (5%). The results are presented in table 4.

TABLE 4

Effect of embryo-peptides from drone larvae, concentrated in ultrafiltrate dialysate, on the growth and mortality of fibroblast cell ICP-23 ($23^{th}$ passage in vitro).

| Experimental variant | Cell number ($x^4$ at $10/cm^2$) | | The mortality. (%) | |
|---|---|---|---|---|
| | 72 h | 96 h | 72 h | 96 h |
| Standard (BME with Eagle 10% fetal bovine serum) | 12.44a | 13.58c | 4.35e | 5.19g |
| Eagle BME with 5% fetal bovine serum + 1% embryo-peptides | 11.32ab | 12.24cd | 3.39f | 4.10h |
| Control (Eagle BME with 5% fetal bovine serum) | 10.12b | 10.58d | 3.86ef | 4.69gh |

* Values followed by the same letter does not differ significantly for $P < 0.05\%$ Embryo-peptides from drone larvae, concentrated in ultrafiltrate dialysate, shown also a cytostimulating and cytoprotective action on human fibroblasts (ICP-line passage $23^{th}$ in vitro). As in the case of other embryo-peptides derived from the first stages of development of insects their biological activity on human cells is less pronounced, as compared with that of the embryo-peptides from chicken embryos. After 96 hours cell number is higher with approx. 12% (BME 5 Eagle with 5% fetal bovine serum—$10.12 \times 10^4$ cells/$cm^2$, Eagle BME with 5% fetal bovine serum+1% embryo-peptides, $11.32 \times 10^4$ cells/$cm^2$). At the same time at 96 hours mortality of treated cells with embryo-peptides (4.10) is 78.9% of mortality is present at the standard 10% fetal bovine serum (5.19%).

In order to compensate this difference of biological activity in the process of obtaining embryonic extracts based on composition of drone larvae has been proceeded to doubling the concentration of the embryo-peptides with molecular weight >10 kDa, ultrafiltrate dialysate.

Product obtained by applying this example has the following characteristics:
- appearance: fine powder, corresponding to the provisions of International Pharmacopoeia;
- color: white-yellowish to pale green;
- smell: characteristic;
- taste: specific, with a slight sweet taste;
- humidity (loss by drying at 105° C. for 4 hours): max. 6%;
- protein content (as total nitrogen×6.25): 10%
- peptides (acid-soluble, with Folin-Ciocâlteu reagent): 20 mg/g;
- total selenium content: min. 15 mg/kg;
- total chromium content: min. 12.5 mg/kg;
- total zinc content: min. 0.19%
- pyridoxine content: min. 0.19%

The composition obtained following the application of invention embodiments form the above examples were tested on lots of 40 young Wistar rats (20 males weighing 97±4 g and 20 females of 95±5 g). Rats were fed with standard diet. The above compositions were administered orally, as 50 mg/kg bodyweight/day, for 60 days. At the end of the experimental period were collected urine and blood and have been determined urinary 17-ketosteroids, total cholesterol and total lipids. The experiment was done with a standard obtained by spray-drying of a mixture obtained by homogenization of the 20 parts of fertilized eggs embryonated for 10 days, containing the embryos of chickens, vitellus and egg white, with 80 parts of maltodextrin, 2 parts of selenium yeast containing 750 mg per kg, 1.5 parts of chromium yeast containing 900 mg Cr per kg, 0.2 parts vitamin $B_6$ (pyridoxine), 0.01 ... 0.015 parts expanded silicon dioxide, 0.01 ... 0.015 parts magnesium stearate 0.01 ... 0.015 methylparaben and 0.005 parts ... 0.010 parts propylparaben. Also included was included a control group, that received only maltodextrin. The results are presented in table 5.

TABLE 5

Action of the compositions according examples 1-3 on some biochemical parameters of laboratory animals.

| Experimental treatment | 17-ketosteroids (mg/g creatinine) | Total cholesterol (mg/dl) | Total lipids (mg/dl) |
|---|---|---|---|
| Control, females | 0.16 ± 0.05 | 88.2 ± 4.0 | 189.3 ± 16.2 |
| Control, males | 0.11 ± 0.03 | 116.7 ± 5.3 | 226.4 ± 12.8 |
| Standard, females | 0.28 ± 0.05* | 86.4 ± 7.2 | 194.3 ± 15.6 |
| Standard, male | 0.19 ± 0.04* | 111.6 ± 7.4 | 216.4 ± 16.4 |
| Product e.g. 1 females | 0.58 ± 0.07*** | 76.2 ± 4.6* | 169.3 ± 16.2* |
| Product e.g. 1 males | 0.32 ± 0.08** | 105.7 ± 2.6* | 194.3 ± 10.2 |
| Product e.g. 2 females | 0.36 ± 0.05** | 92.6 ± 8.3 | 189.3 ± 16.2 |
| Product e.g. 2 males | 0.27 ± 0.06** | 114.6 ± 9.4 | 226.4 ± 12.8 |
| Product e.g. 3 females | 0.42 ± 0.07** | 87.5 + 12.4 | 189.3 ± 16.2 |
| Product e.g. 3 males | 0.28 ± 0.05** | 118.9 ± 8.3 | 226.4 ± 12.8 |

*Significant, p < 0.05;
*Very significant, p < 0.01;
*Highly significant, P < 0.001

These results demonstrate that embryo extracts stimulates steroidogenesis, all products, including the standard one determining an increased production of urinary 17-ketosteroids. The main precursors of 17-ketosteroids are dehydroepiandrosterone (DHEA) and dehydroepiandrosterone sulfate (DHEA-S) and other adrenal cortical hormones, thus oral administration of embryonic extracts stimulate the hypothalamic-pituitary-adrenal axis, most probably due to the paracrine/autocrine action of embryo-peptides with growth factors activity.

The results also demonstrate in a convincingly manner the bioavailability increase of embryo-peptides orally administrated, on the compositions done according to the invention.

Because the composition obtained according to example 1, based on embryo-peptides extracted from chicken embryo, present the most significant effects on laboratory animal, only this composition was tested also on human subjects.

The first experiment was conducted on 30 young healthy athletes (rugby players), who participated in the study as volunteers. They were divided into lots of 10 subjects. The first lot received capsules filled with maltodextrin (placebo). To the second lot were administered 4 capsules a day, each of 500 mg, administered 2 capsules one hour after breakfast and 2 capsules one hour after lunch. The third group received 8 capsules a day, 4 capsules one hour after breakfast and 4 capsule one hour after lunch. The treatment was done for 60 days. On each human subject was determined the level of steroid hormones (DHEA, DHEA-sulphate, testosterone, androstenedione). The results are presented in table 6.

TABLE 6

Effect of oral administration for 60 days of the composition done according to Ex. 1, from chicken embryos, on the level of certain hormones from the serum of young athletes.

| | Experimental treatment | | |
|---|---|---|---|
| Hormone | Placebo | 4 capsules/day | 8 capsules/day |
| DHEA | 120.6 ± 15.6 | 98.7 ± 11.2 | 115.2 ± 13.8 |
| DHEA-sulfate | 84.3 ± 12.4 | 111.5 ± 10.5 | 107.5 ± 10.4 |
| Androstenedione | 87.5 ± 14.1 | 138.8 ± 20.8 | 126.5 ± 16.4 |
| Testosterone | 101.4 ± 15.1 | 127.3 ± 16.6 | 137.4 ± 19.6 |

After the oral administration of the composition of embryo-peptides with increased bioavailability, obtained according to Example 1, have not been significant changes in the levels of DHEA and DHEA-sulphate, but significant changes have been identified on the levels of androgen steroid hormones, androstenedione and testosterone. Administration of a double dose of composition done in accordance with the Example 1 has not resulted in additional effects, thus the dose used in the next experiment, conducted on elderly subjects, was only that of 4 capsules per day.

Elderly subjects (32 women and 28 men) were between 55 and 75 years old, with a good health status. On the beginning of the experiment the biochemical parameters (total cholesterol; LDL-cholesterol; HDL-cholesterol levels; 17-cetosteroizi; cortisol) were determined for each sex. The subjects were then randomly divided into two groups, one that received a placebo (a capsule filled with maltodextrin) and another on that receive the composition done in accordance with example 1, 4 capsules a day, each of 500 mg, administered 2 capsules one hour after breakfast and 2 capsules one hour after lunch. After 60 days of oral administration were determined once again the same biochemical parameters. The results are presented in table 7.

TABLE 7

Influence of oral administration for 60 days the composition made according to Ex 1 from chicken embryos, on some biochemical parameters of elderly subjects.

| Experimental version | | Total cholesterol (mg/dl) | LDL-cholesterol (mg/dl) | HDL-cholesterol (mg/dl) | 17-Ketosteroids (mg/24 h) | Cortisol (nmol/l) |
|---|---|---|---|---|---|---|
| Men | Initially | 248.4 ± 6.3 | 156.5 ± 5.3 | 45.2 ± 8.4 | 27.9 ± 4.8 | 486.5 ± 24.2 |
| | 4. caps/day ex. 1 composition | 216.6 ± 94.4** | 117.6 ± 8.5** | 54.2 ± 7.8* | 33.5 ± 4.2* | 373.6 ± 28.7* |
| | Placebo | 243.5 ± 7.4 | 154.3 ± 8.1 | 48.6 ± 9.2 | 29.2 ± 7.4 | 478.4 ± 24.8 |
| Women | Initially | 274.6 ± 4.3 | 174.8 ± 4.3 | 48.6 ± 10.2 | 23.7 ± 5.6 | 26.2 ± 475.8 |
| | 4. caps/day care instructions 1. | 234.5 ± 9.2* | 140.6 ± 7.2** | 59.8 ± 8.4* | 27.2 ± 5.4 | 418.5 ± 25.6* |
| | Placebo | 262.6 ± 8.9 | 184.8 ± 5.8 | 47.2 ± 9.7 | 24.8 ± 4.2 | 457.8 ± 32.6 |

*Significant, $p < 0.05$;
*Very significant, $p < 0.01$;

Composition with increased bioavailability of orally administrated embryo-peptides obtained in accordance with this invention, when is administrated as dietary supplement in dose of 2 capsules one hour after breakfast and 2 capsules one hour after lunch, for a period of a minimum 60 days, re-equilibrate the metabolism, normalize cortisol level, decreased total triglyceride, total cholesterol and its low-density lipoprotein fraction and increased the heavy density lipoprotein fraction of cholesterol on healthy human subjects of third age.

The invention claimed is:

1. A method for producing a composition comprising embryo-peptides for oral administration, comprising the following steps:
   a) harvesting vitellus, egg white, and a biological material comprising chicken embryos, together with chorioallantoic membranes, from chicken eggs fertilized and incubated for 10 days;
   b) producing an embryonic extract by a process comprising:
      i) disintegrating the biological material using a colloidal mill and determining the dry matter content of the biological material by refractometry;
      ii) diluting 10 parts of disintegrated embryos, expressed as dry matter, with 90 parts of sterile distilled water;
      iii) homogenizing the diluted disintegrated embryos to produce a suspension;
      iv) mixing 100 parts of the suspension with 1.25 parts zinc carbonate followed by removal of excess zinc carbonate and cellular debris by centrifugation;
      v) filtering the suspension through a 10 kDa membrane to produce embryo-proteins having a molecular weight >10 kDa and embryo-peptides having a molecular weight <10 kDa;
      vi) denaturing the embryo-proteins by heating at 85° C. for 25 min;
      vii) mixing the embryo-peptides and denatured embryo-proteins back together at a 1 to 9 ratio to produce the embryonic extract;
   c) obtaining cationic peptides by a process comprising:
      i) enzymatically hydrolyzing 100 parts vitellus and egg white with 2 parts serine-endopeptidase,
      ii) filtering the hydrosylate for peptides with a molecular weight of less than 10 kDa, and
      iii) purifying the peptides with an ion exchange resin to produce cationic peptides;
   d) producing a mixture comprising
      20 parts of embryonic extract,
      0.5 parts of the cationic peptides,
      80 parts maltodextrin,
      2 parts selenium yeast containing 750 mg Se per kg,
      1.5 part chromium yeast containing 900 mg Cr per kg,
      0.2 parts vitamin B6, pyridoxine,
      0.5 parts of sodium taurocholate,
      from 0.01 to 0.015 parts of expanded silicon dioxide,
      from 0.01 to 0.015 parts of magnesium stearate,
      from 0.01 to 0.015 parts of methylparaben, and
      from 0.005 parts to 0.010 parts of propylparaben;
   e) homogenizing the mixture; and
   f) spray-drying the homogenized mixture, at a rate of max. 10 kg/h, using a centrifugal atomizer operated at about 20,000 rpm, at an air inlet temperature of from 140 to 150° C. and an air outlet temperature of from 80 to 85° C.,
   parts being expressed in units of weights.

2. A composition comprising embryo-peptides produced by the method of claim 1.

3. The method of claim 1, wherein the serine-endopeptidase comprises a specific enzymatic activity of 1.5 units Anson (AU) per gram.

4. A method for producing a composition comprising embryo-peptides for oral administration, comprising the following steps:
   a) harvesting 7 day old drone brood/male larvae of *Apis melifera*, at 10 days after haploid eggs laying to produce a biological material;
   b) producing an embryonic extract by a process comprising:
      i) disintegrating the biological material using a colloidal mill and determining the dry matter content of the biological material by refractometry;
      ii) diluting 10 parts of disintegrated embryos, expressed as dry matter, with 90 parts of sterile distilled water;
      iii) homogenizing the diluted disintegrated embryos with a piston homogenizer at high pressure, two cycles at 50 MPa to produce a suspension;
      iv) mixing 100 parts of the suspension with 1.25 parts zinc carbonate followed by removal of excess zinc carbonate and cellular debris by centrifugation;
      v) filtering the suspension through a 10 kDa membrane to produce embryo-proteins having a molecular weight >10 kDa and embryo-peptides having a molecular weight <10 kDa;

vi) denaturing the embryo-proteins by heating at 85° C. for 25 min;

vii) mixing the embryo-peptides and denatured embryo-proteins back together at a 1 to 4 ratio to produce the embryonic extract;

c) obtaining cationic peptides by a process comprising:
   i) enzymatically hydrolyzing 100 parts chicken vitellus and egg white with 2 parts serine-endopeptidase,
   ii) filtering the hydrosylate for peptides with a molecular weight of less than 10 kDa, and
   iii) purifying the peptides with an ion exchange resin to produce cationic peptides;

d) producing a mixture comprising
   20 parts of embryonic extract,
   0.5 parts of the cationic peptides,
   80 parts maltodextrin,
   2 parts selenium yeast containing 750 mg Se per kg,
   1.5 part chromium yeast containing 900 mg Cr per kg,
   0.2 parts vitamin B6, pyridoxine,
   0.5 parts of sodium taurocholate,
   from 0.01 to 0.015 parts of expanded silicon dioxide,
   from 0.01 to 0.015 parts of magnesium stearate,
   from 0.01 to 0.015 parts of methylparaben, and
   from 0.005 parts to 0.010 parts of propylparaben;

e) homogenizing the mixture by using a piston homogenizer at high pressure, 2 cycles at 35 MPa; and f) spray-drying the homogenized mixture, at a rate of max. 10 kg/h, using a centrifugal atomizer operated at 20,000 rpm, at an air inlet temperature of from 140 to 150° C. and an air outlet temperature of from 80 to 85° C., parts being expressed in units of weights.

5. A composition comprising embryo-peptides produced by the method of claim 4.

6. A method for producing a composition comprising embryo-peptides for oral administration, comprising the following steps:

a) disinfecting silkworm non-diapause eggs to produce a biological material;

b) producing an embryonic extract by a process comprising:
   i) disintegrating the biological material using a colloidal mill and determining the dry matter content of the biological material by refractometry;
   ii) diluting 10 parts of disintegrated embryos, expressed as dry matter, with 90 parts of sterile distilled water;
   iii) homogenizing the diluted disintegrated embryos with a piston homogenizer at high pressure, two cycles at 50 MPa to produce a suspension;
   iv) mixing 100 parts of the suspension with 1.25 parts zinc carbonate followed by removal of excess zinc carbonate and cellular debris by centrifugation;
   v) filtering the suspension through a 10 kDa membrane to produce embryo-proteins having a molecular weight >10 kDa and embryo-peptides having a molecular weight <10 kDa;
   vi) denaturing the embryo-proteins by heating at 85° C. for 25 min;
   vii) mixing the embryo-peptides and denatured embryo-proteins back together at a 1 to 4 ratio to produce the embryonic extract;

c) obtaining cationic peptides by a process comprising:
   i) enzymatically hydrolyzing 100 parts chicken vitellus and egg white with 2 parts serine-endopeptidase,
   ii) filtering the hydrosylate for peptides with a molecular weight of less than 10 kDa, and
   iii) purifying the peptides with an ion exchange resin to produce cationic peptides;

d) producing a mixture comprising
   20 parts of embryonic extract,
   0.5 parts of the cationic peptides,
   80 parts maltodextrin,
   2 parts selenium yeast containing 750 mg Se per kg,
   1.5 part chromium yeast containing 900 mg Cr per kg,
   0.2 parts vitamin B6, pyridoxine,
   0.5 parts of sodium taurocholate,
   from 0.01 to 0.015 parts of expanded silicon dioxide,
   from 0.01 to 0.015 parts of magnesium stearate,
   from 0.01 to 0.015 parts of methylparaben, and
   from 0.005 parts to 0.010 parts of propylparaben;

e) homogenizing the mixture by using a piston homogenizer at high pressure, 2 cycles at 35 MPa; and f) spray-drying the homogenized mixture, at a rate of max. 10 kg/h, using a centrifugal atomizer operated at 20,000 rpm, at an air inlet temperature of from 140 to 150° C. and an air outlet temperature of from 80 to 85° C., parts being expressed in units of weights.

7. A composition comprising embryo-peptides produced by the method of claim 6.

* * * * *